US012758352B2

(12) United States Patent
Wang

(10) Patent No.: US 12,758,352 B2
(45) Date of Patent: Oct. 13, 2026

(54) POSITIONING MARKER BALL AND METHOD FOR MAKING THE SAME AND POSITIONING DEVICE HAVING THE SAME

(71) Applicant: TAIWAN MAIN ORTHOPAEDIC BIOTECHNOLOGY CO., LTD., Taichung City (TW)

(72) Inventor: Min-Liang Wang, Taichung City (TW)

(73) Assignee: TAIWAN MAIN ORTHOPAEDIC BIOTECHNOLOGY CO., LTD., Taichung City (TW)

( * ) Notice: Subject to any disclaimer, the term of this patent is extended or adjusted under 35 U.S.C. 154(b) by 265 days.

(21) Appl. No.: 18/424,174

(22) Filed: Jan. 26, 2024

(65) Prior Publication Data

US 2025/0064547 A1 Feb. 27, 2025

(30) Foreign Application Priority Data

Aug. 24, 2023 (TW) ................................ 112131902

(51) Int. Cl.
*A61B 90/00* (2016.01)
*A61L 31/02* (2006.01)
(Continued)

(52) U.S. Cl.
CPC ............ *A61B 90/39* (2016.02); *A61L 31/022* (2013.01); *A61L 31/14* (2013.01); *B29D 11/0073* (2013.01); *B32B 1/00* (2013.01); *B32B 7/12* (2013.01); *B32B 27/08* (2013.01); *B32B 27/18* (2013.01); *B32B 27/36* (2013.01); *A61B 2090/3937* (2016.02);
(Continued)

(58) Field of Classification Search
CPC ..................................................... A61B 90/39
See application file for complete search history.

(56) References Cited

U.S. PATENT DOCUMENTS 7,874,686 B2 * 1/2011 Rossner ................ B29C 70/585 359/530
2016/0306083 A1 * 10/2016 Huldin ................... G02B 5/134
2019/0209080 A1 * 7/2019 Gullotti ............. A61B 17/7035

FOREIGN PATENT DOCUMENTS

CN 201067403 Y 6/2008
CN 212547885 U 2/2021
(Continued)

OTHER PUBLICATIONS

English translation of CN 201067403 Y (Year: 2008).*
(Continued)

*Primary Examiner* — Erin McGrath
(74) *Attorney, Agent, or Firm* — MUNCY, GEISSLER, OLDS & LOWE, P.C.

(57) ABSTRACT

A positioning marker ball is adapted for an optical positioning system and includes a main body unit, and an optical unit. The main body unit includes a ball body, and a rod portion that extends outwardly from the ball body, and that has a connecting end section disposed opposite the ball body and is adapted to connect a mount. The ball body is molded integrally with the rod portion. The optical unit is disposed on the ball body, and includes a reflective layer that is disposed on the ball body to reflect light. A positioning device adapted for an optical positioning system includes the positioning marker ball described above. A method for making the positioning marker ball is also included.

11 Claims, 16 Drawing Sheets

(51) Int. Cl.

| | |
|---|---|
| ***A61L 31/14*** | (2006.01) |
| ***B29D 11/00*** | (2006.01) |
| ***B32B 1/00*** | (2006.01) |
| ***B32B 7/12*** | (2006.01) |
| ***B32B 27/08*** | (2006.01) |
| ***B32B 27/18*** | (2006.01) |
| ***B32B 27/36*** | (2006.01) |
| *B29K 67/00* | (2006.01) |
| *B29K 509/08* | (2006.01) |
| *B29K 705/02* | (2006.01) |

(52) U.S. Cl.

CPC .... *B29K 2067/003* (2013.01); *B29K 2509/08* (2013.01); *B29K 2705/02* (2013.01); *B32B 2255/10* (2013.01); *B32B 2255/205* (2013.01); *B32B 2264/101* (2013.01); *B32B 2307/412* (2013.01); *B32B 2307/416* (2013.01); *B32B 2535/00* (2013.01); *B32B 2551/00* (2013.01)

(56) References Cited

FOREIGN PATENT DOCUMENTS

| | | | |
|---|---|---|---|
| CN | 115153843 | A | 10/2022 |
| CN | 217938396 | U | 12/2022 |
| CN | 116077185 | A | 5/2023 |
| CN | 219184092 | U | 6/2023 |

OTHER PUBLICATIONS

Search Report appended to an Office Action, which was issued to Taiwanese counterpart application No. 112131902 by the TIPO on Dec. 7, 2023, with an English translation thereof.

* cited by examiner

POSITIONING MARKER BALL AND METHOD FOR MAKING THE SAME AND POSITIONING DEVICE HAVING THE SAME

CROSS-REFERENCE TO RELATED APPLICATION

This application claims priority to Taiwanese Invention patent application Ser. No. 11/213,1902, filed on Aug. 24, 2023, and incorporated by reference herein in its entirety.

FIELD

The disclosure relates to a positioning device for an optical positioning and tracking system, more specifically to a positioning device that uses a positioning marker ball and a method for making the same.

BACKGROUND

Surgical navigation technology integrates diagnostic information, image data, and positioning information to provide instrument tracking for surgeons which increases surgical precision, decreases the risk of surgical errors, reduces operating time, and improves surgical outcomes.

Positioning marker balls are optical positioning devices used to track positioning and speed of surgical instruments. A computer integrates image processing and equipment such as robotic arms via a surgical navigation software to precisely guide surgical equipment towards the target site, thereby increasing surgical accuracy and has the added benefit of reducing operating time.

Referring to FIG. 1, a conventional positioning device 9 for optical surgical navigation disclosed in Chinese Utility Model Patent Publication No. CN201067403Y includes a positioning rigid mount 91, a plurality of attachment studs 92, and four positioning balls 93. The positioning rigid mount 91 has a cross layout. The four positioning balls 93 are press fitted to the attachment studs 92. Because the positioning balls 93 are attached to the attachment studs 92 in a press fit, manufacturing tolerances often lead to a loose fitting between the positioning balls 93 and the attachment studs 92, and cause rattling and separation of the positioning balls 93. Therefore, there is room for improvement of the conventional positioning device 9.

SUMMARY

Therefore, an object of the disclosure is to provide a positioning marker ball, a positioning device, and a method for making the positioning marker ball that can alleviate at least one of the drawbacks of the prior art.

According to a first aspect of the disclosure, the positioning marker ball is adapted for an optical positioning and tracking system and includes a main body unit, and an optical unit. The main body unit includes a ball body, and a rod portion that extends outwardly from the ball body, and that has a connecting end section disposed opposite the ball body and is adapted to connect a mount. The ball body is molded integrally with the rod portion. The optical unit is disposed on the ball body, and includes a reflective layer that is disposed on the ball body, and that reflects light.

According to another aspect of the disclosure, the positioning device is adapted for an optical positioning and tracking system and includes a mount including a plurality of threaded holes, and a plurality of positioning marker balls each of which is the positioning marker ball according to the first aspect of the disclosure. The connecting end portion of each of the positioning marker balls is coupled with one of the threaded holes of the mount.

According to a third aspect of the disclosure, the method for making a positioning marker ball adapted for an optical positioning and tracking system includes the steps of: preparing a plastic shape setting film and an optical film stack that has a plurality of optical elements spread thereon; forming first and second reflective shells which includes a step of binding together the plastic shape setting film and the optical film stack to form a laminate, and a step of shaping the laminate, each of the first and second reflective shells having a predesignated shape; preparing a main body unit that has a ball body, and a rod portion that extends outwardly from the ball body; enwrapping the ball body of the main body unit with the first and second reflective shell to form a positioning marker ball, while exposing the rod portion of the main body unit; wherein the positioning marker ball has an optical layer disposed on the ball body, a reflective layer that is formed between the ball body and the optical layer, and that reflects light, and a shape setting layer that is formed between the optical layer and the ball body, the shape setting layer being formed from the plastic shape setting film, the optical layer and the reflective layer being formed from the optical film stack.

According to a fourth aspect of the disclosure, a positioning marker ball includes a main body unit, and an optical unit. The main body unit includes a ball body that is transparent and hollow, and a rod portion that extends outwardly form the ball body, and that has a connecting end portion disposed opposite to the ball body and adapted to connect a mount. The ball body is molded integrally with the rod portion. The rod portion is hollow and has a passage hole spatially communicating an interior of the ball body. The optical unit has a light source mounted inside the ball body of the main body unit and adapted to connect a power source through the passage hole.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
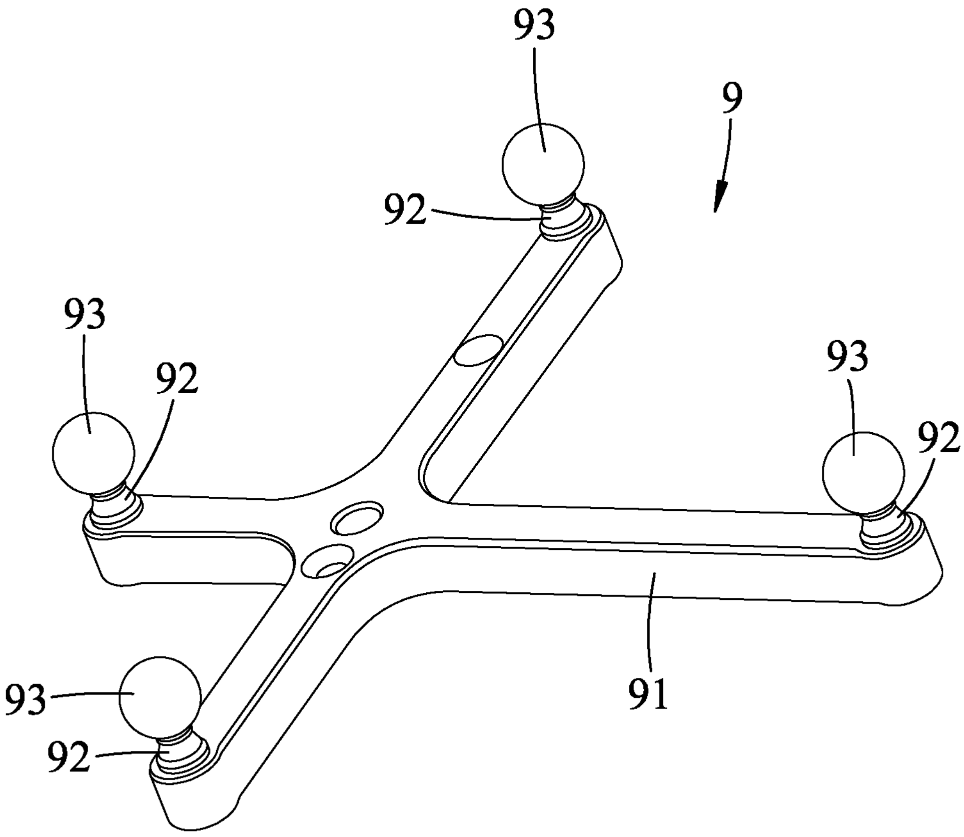
FIG. 1 PRIOR ART
FIG. 1 is a perspective view illustrating a conventional positioning device for optical surgical navigation disclosed in Chinese Utility Model Patent Publication No. CN201067403Y.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

Figure 2:
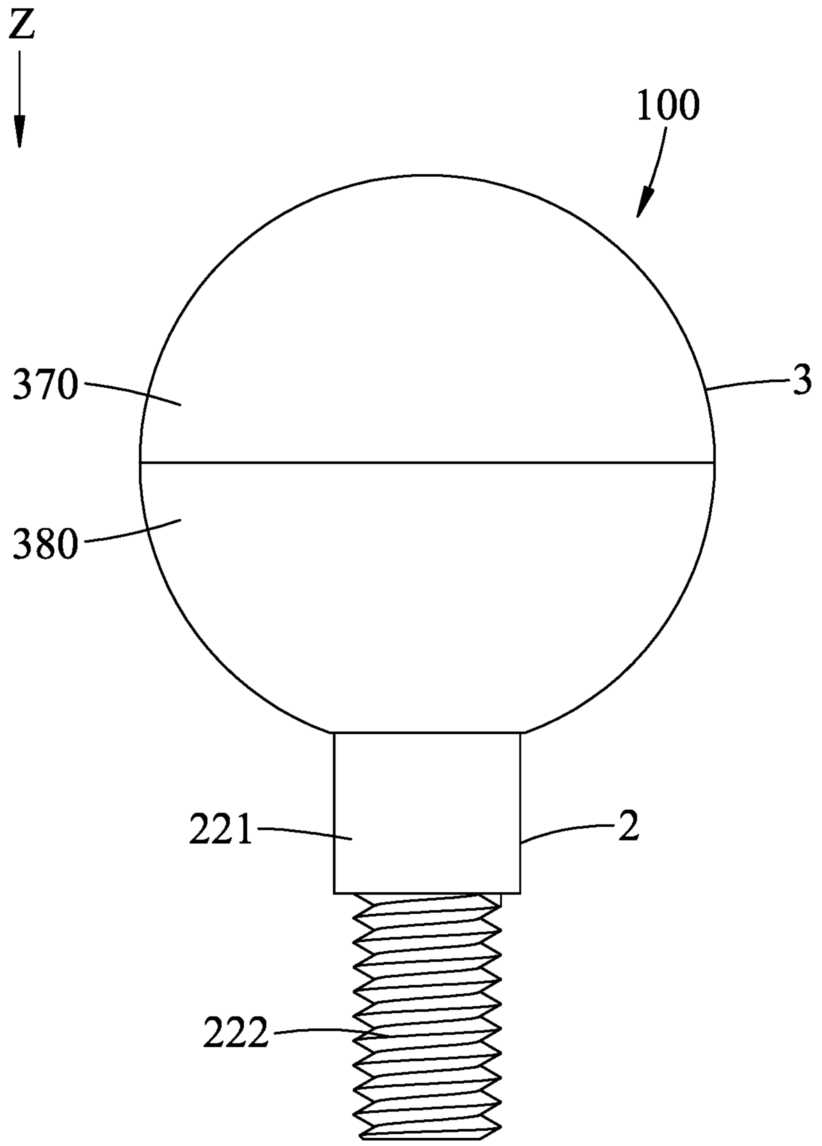
FIG. 2 is a side view illustrating a first embodiment of a positioning marker ball adapted for an optical positioning system according to the present disclosure.
Figure 3:
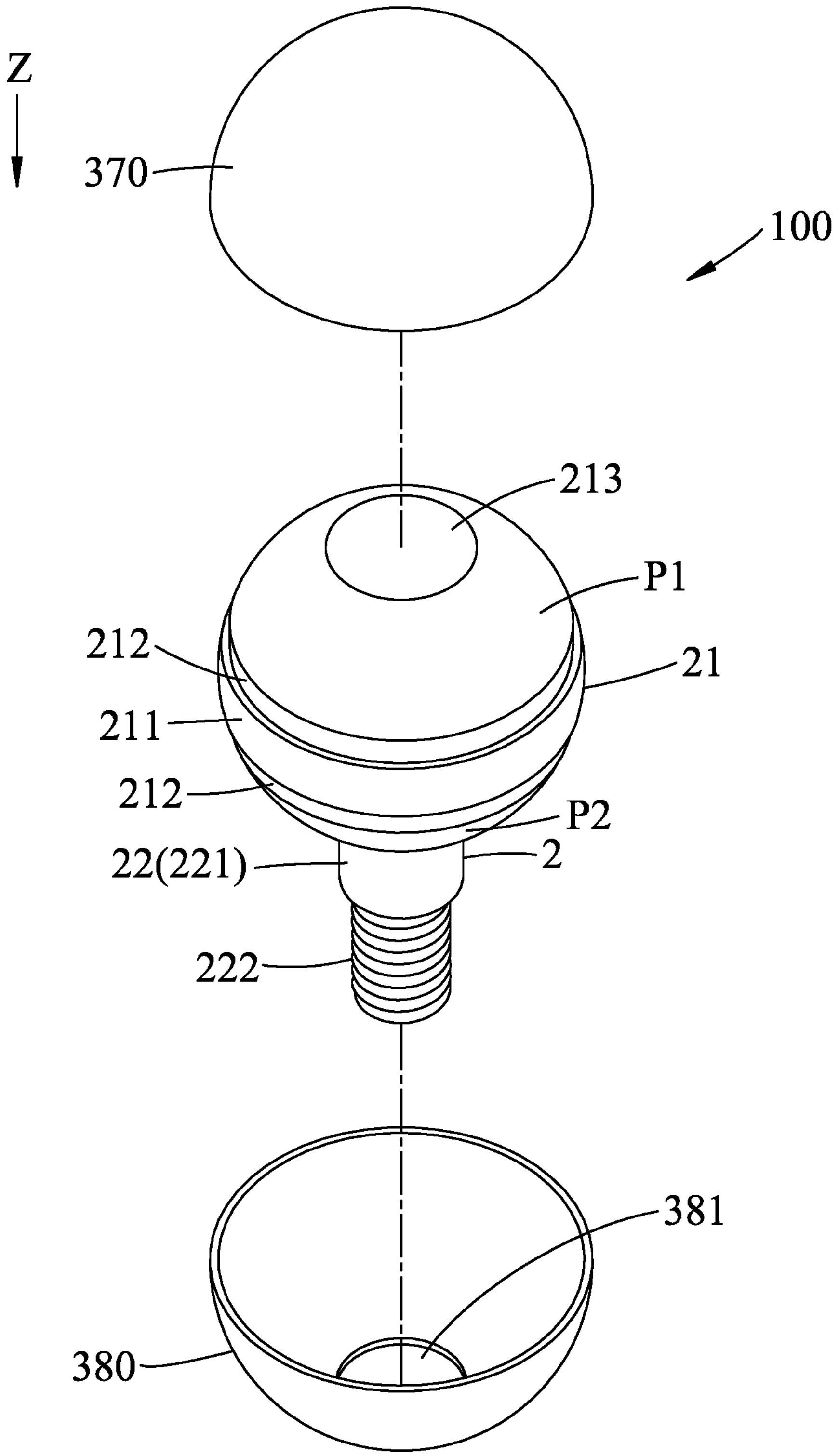
FIG. 3 is an exploded perspective view illustrating the first embodiment.
Figure 4:
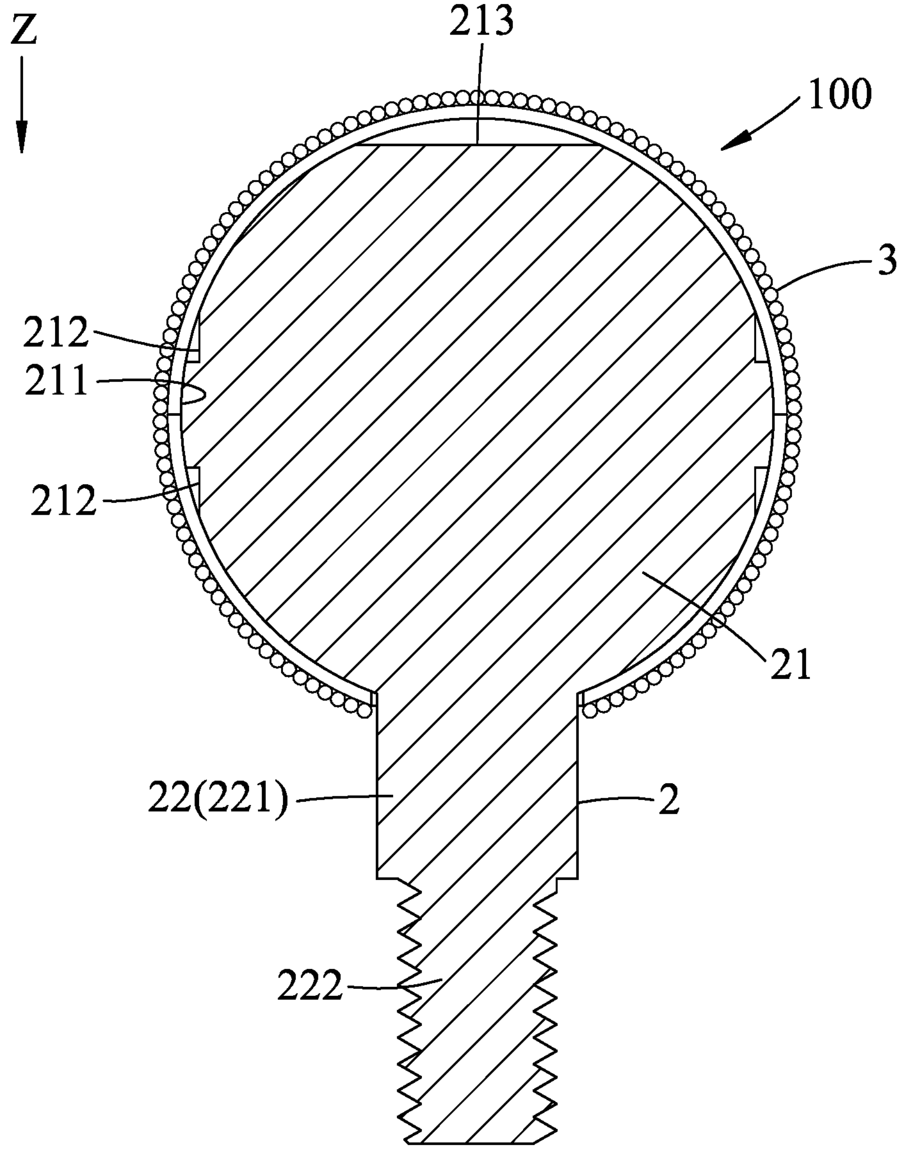
FIG. 4 is a cross-sectional view illustrating the first embodiment.

Referring to FIGS. 2 to 4, a first embodiment of a positioning marker ball 100 adapted for an optical positioning and tracking system according to the present disclosure includes a main body unit 2 and an optical unit 3. The main body unit 2 includes a ball body 21 and a rod portion 22. In this embodiment, the main body unit 2 is entirely made of aluminum or an aluminum alloy, and the ball body 21 and the rod portion 22 are formed integrally by molding. The ball body 21 is a solid core that has a roughly spherical shape, and the rod portion 22 extends outwardly from the ball body 21 in a downward direction (Z) and is in line with an axial line of the ball body 21. The ball body 21 has an equatorial line 211, two depressions 212, and a top surface 213. The equatorial line 211 divides an outer surface of the ball body 21 into a first portion (P1) (which will be referred to as an upper half (P1) hereinafter) and a remaining second portion (P2) (which will be referred to as a lower half (P2) hereinafter). The depressions 212 are respectively located above and below the equatorial line 211 on opposite sides of the equatorial line 211. The depressions 212 sink inwardly from the outer surface of the ball body 21 and are respectively formed in the upper half (P1) and the lower half (P2) near the equatorial line 211 respectively. The top surface 213 is flat and formed on a top portion of the ball body 21 opposite to the rod portion 22. The rod portion 22 extends outwardly and downwardly from the ball body 21 and is in line with an axial line of the ball body 21. The rod portion 22 has a circular cross section and has an interconnecting section 221 and a connecting end section 222. The interconnecting section 221 is opposite to the connecting end section 222 and is interconnected with the ball body 21. The connecting end section 222 extends outwardly in the direction (Z) from the interconnecting section 221 and is disposed opposite to the ball body 21 and adapted to connect a mount. The connecting end section 222 has a diameter that is less than the interconnecting section 221. In the first embodiment, the connecting end section 222 has a threaded outer surface. In this embodiment, the main body unit 2 is easy to manufacture and has low manufacturing costs because the ball body 21 has a solid core which simplifies manufacturing processes. However, this is not a limitation of the disclosure and in other embodiments, the ball body 21 may have a hollow core and be made of other materials.

Figure 5:
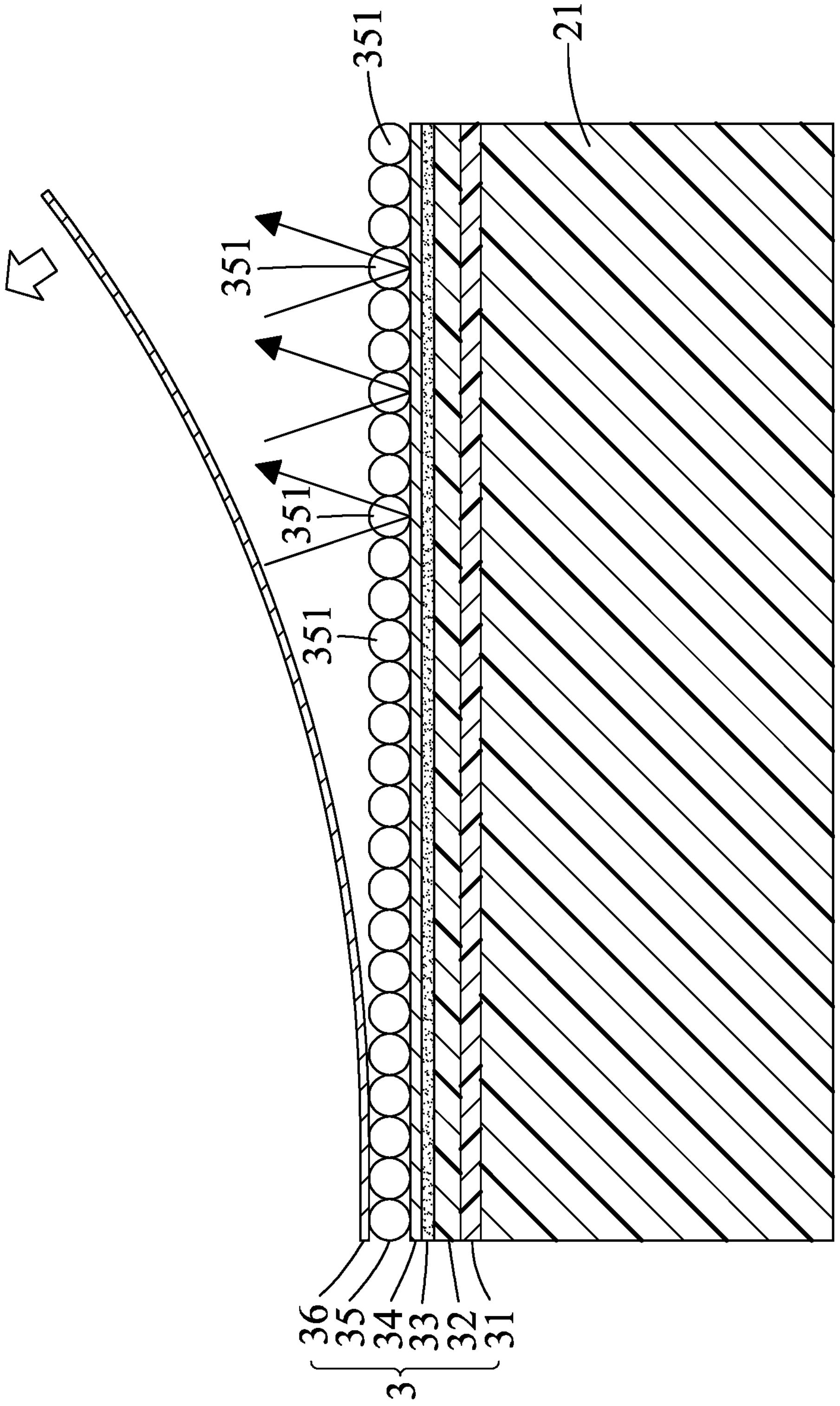
FIG. 5 is a fragmentary enlarged cross-sectional view illustrating an optical unit of the positioning marker ball.

Referring to FIGS. 4 and 5, the optical unit 3 is disposed on the ball body 21, and includes an adhesive layer 31, a shape setting layer 32, a back adhesive layer 33, a reflective layer 34, an optical layer 35, and a release layer 36, which are stacked on the ball body 21 in the described order and in an outward direction from the ball body 21. Referring back to FIGS. 2 and 3, the optical unit 3 includes a first reflective shell 370 covering and adhesively bonded to a first portion (P1) of an outer surface of the ball body 21, and a second reflective shell 380 covering and adhesively bonded to a remaining second portion (P2) of the ball body 21. The first and second reflective shells 370, 380 are convex and complementarily form a ball-shaped shell. Each of the first and second reflective shells 370, 380 has the reflective layer 34 that is disposed on the ball body, the optical layer 35 that is laminated with the reflective layer 35 and disposed between the optical layer and the ball body and that has a plurality of optical transparent elements 351, and the shape setting layer 32 that is disposed between the reflective layer 34 and the ball body 21.

The adhesive layer 31 shown in FIG. 5 can be cured at a normal temperature. The shape setting layer 32 may be made of a hard plastic material such as polyethylene terephthalate (PET) and disposed on the adhesive layer 31; however, this is not a limitation of the disclosure, and in other embodiments, the shape setting layer 32 may be made of thermal plastic material. The back adhesive layer 33 is made of an adhesive material and disposed on the shape setting layer 32. The reflective layer 34 is a metallic coated layer made of molten aluminum with high light reflecting qualities and is disposed on the back adhesive layer 33. The optical layer 35 is disposed on the reflective layer 34 and includes a plurality of optical elements 351 that allow passage of light therethrough. The optical elements 351 may be electrostatically embedded into a polymer material. In the first embodiment, the optical elements 351 are transparent glass beads with a high reflective index; however, in other embodiments, the optical elements 351 may be transparent plastic beads. When light is incident on an outer surface of the optical elements 351 the light will be refracted to converge on the reflective layer 34, the reflective layer 34 will reflect the light back to the optical elements 351, thereby creating retroreflection and increasing the brightness of the optical elements 351. The release layer 36 that removably covers the optical layer 35 may be peeled off when the optical layer 35 is used; the release layer 36 provides protection from scratching to the optical layer 35. In some embodiments, the optical layer 35 is disposed on an outer surface of the ball body 21, the shape setting layer 32 and the reflective layer 34 are formed between the optical layer 35 and the ball body 21, and the reflective layer 34 reflects light.

The ball body 21 is molded integrally with the rod portion 22. Since the ball body 21 and the rod portion 22 of the main body unit 2 are integrally molded, the ball body 21 will not have problems such as loosening, rattling, falling apart. The ball body 21 is structurally strong which is safer in the surgical environment.

Figure 6:
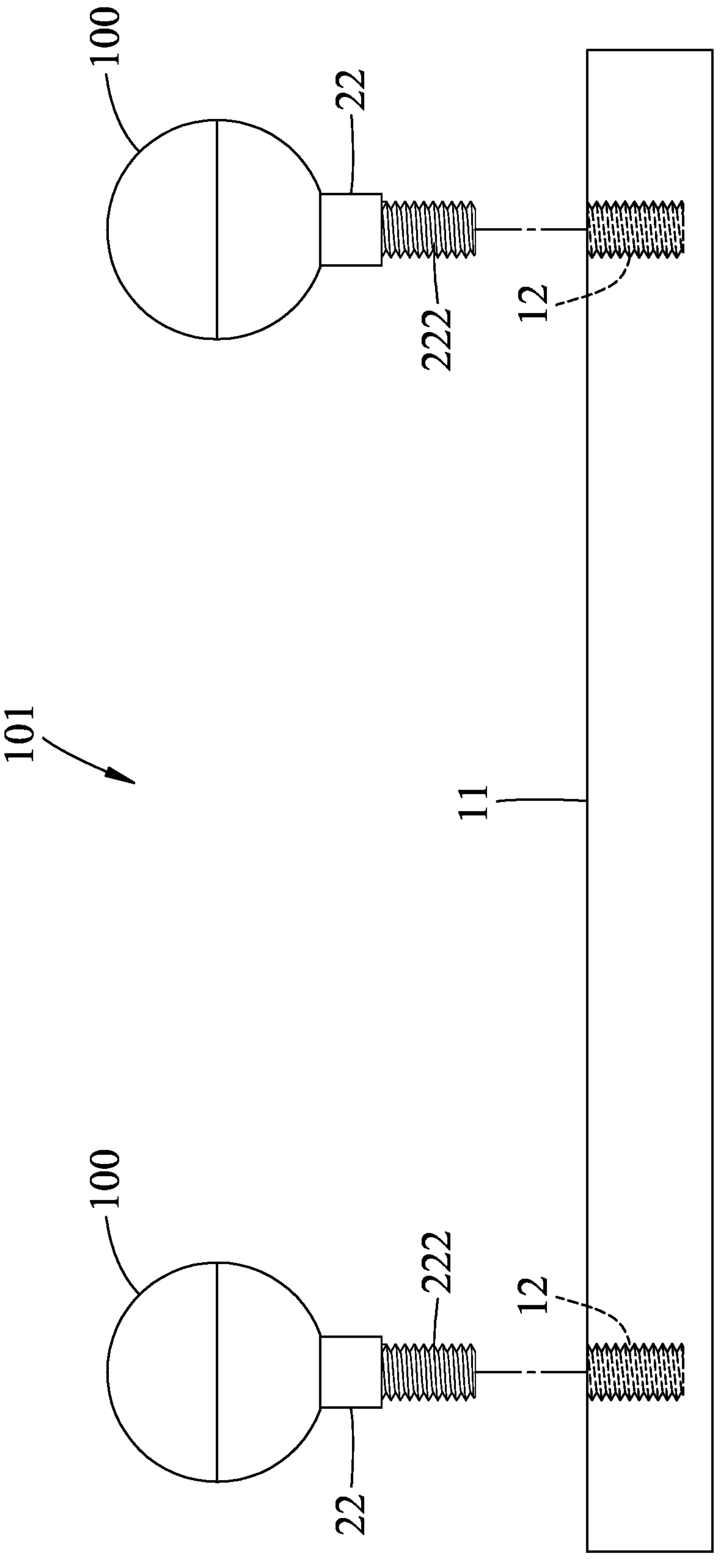
FIG. 6 is a side exploded schematic side view illustrating an embodiment of a positioning device according to the present disclosure.

Referring to FIG. 6, a positioning device 101 is adapted for the optical positioning and tracking system and includes a mount 11 and a plurality of the positioning marker balls 100. The mount 11 is rigid and includes a plurality of threaded holes 12. The connecting end portion 222 of each of the positioning marker balls 100 is coupled with one of the threaded holes 12 of the mount 11. The positioning device 101 helps to accurately track instruments during surgery and helps to improve surgical precision.

Figure 7:
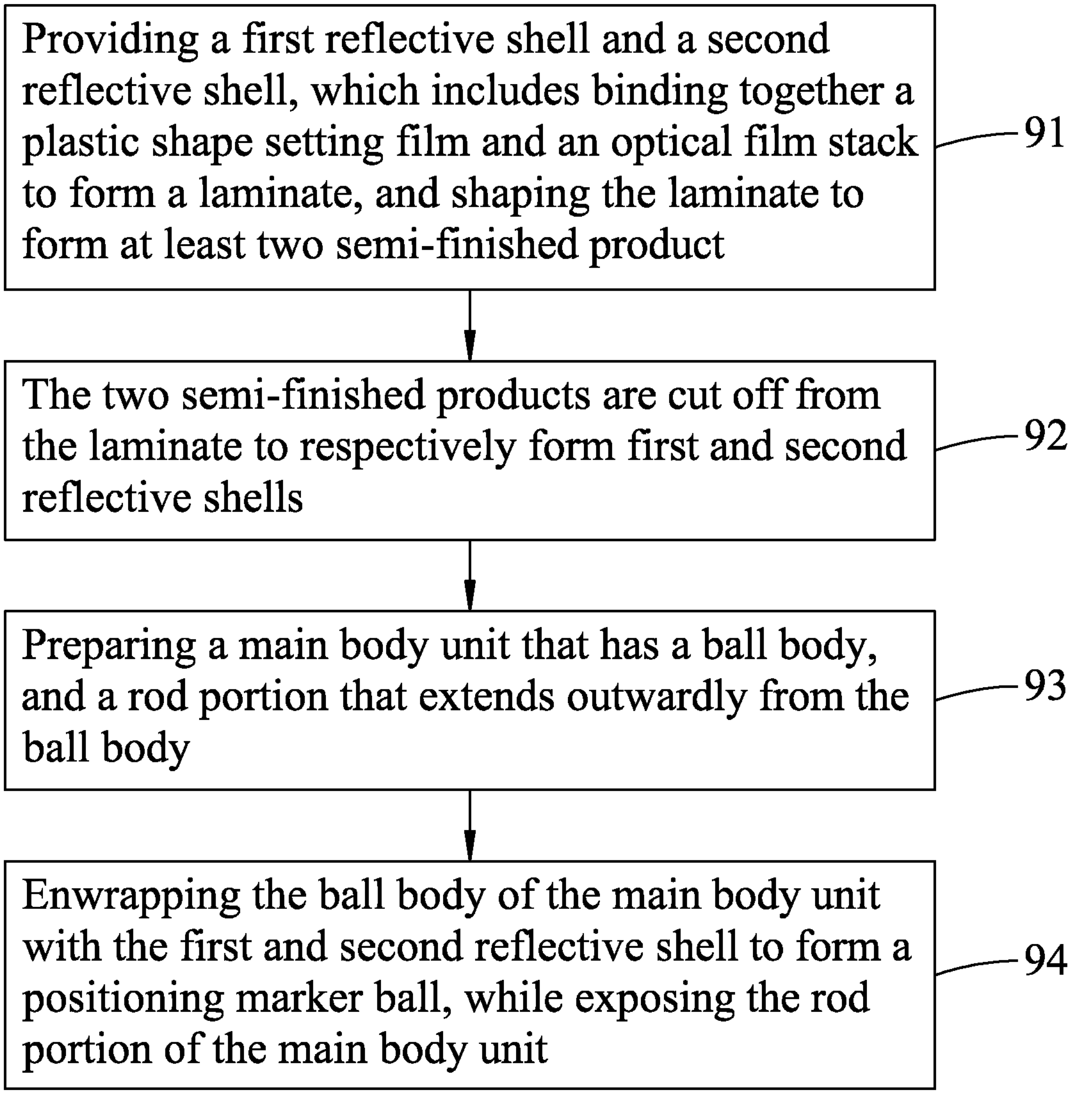
FIG. 7 is a block diagram showing a method for making the positioning marker ball of the first embodiment.

Referring to FIG. 7, a method for making a positioning marker ball 100 of the first embodiment adapted for an optical positioning and tracking system includes the steps 91 to 94.

Figure 8:
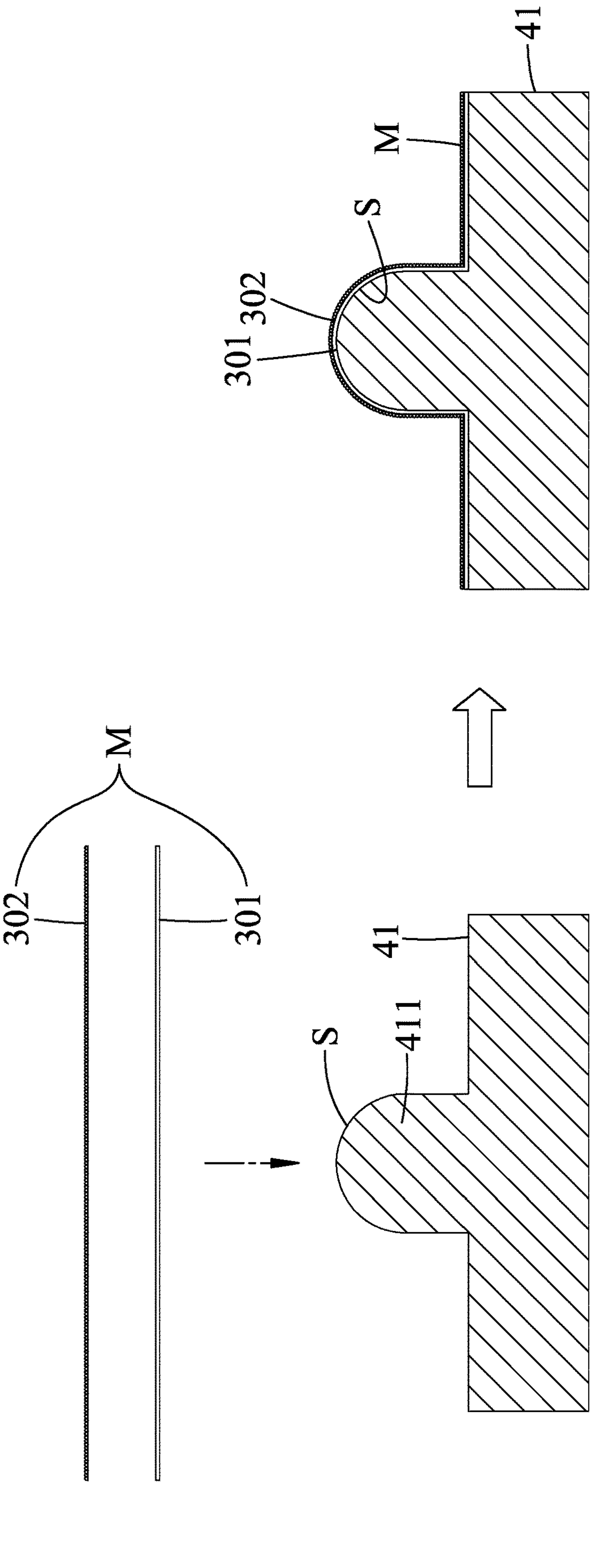
FIGS. 8 to 12 are schematic views illustrating consecutive steps in the method.

In the step 91, referring to FIGS. 7 and 8, a first and second reflective shell 370, 380 are formed by binding together a plastic shape setting film (301) and an optical film stack (302) to form a laminate (M), and shaping the laminate (M). More specifically, a plastic shape setting film 301 and an optical film stack 302 that has a plurality of optical elements 351 distributed thereon are prepared. The plastic shape setting film 301 and the optical film stack 302 are laminated together to form a laminate (M), and the laminate (M) is then shaped to form the first and second reflective shells 370, 380. A mold 41 including a protruding portion 411 is also prepared in this step. The protruding portion 411 has an outer forming surface(S) with a designated convex shape. The optical film stack 302 laminated with the plastic shape setting film 301 is placed above the mold 41, and heated until softened. At the same time, a vacuum is applied to the mold 41 so that the optical film stack 302 and the plastic shape setting film 301 are drawn to the outer forming surface(S) of the protruding portion 411. Because the plastic shape setting film 301 is a thermoplastic film that is pliable when heated, the shape thereof conforms to the predesignated convex shape of the outer forming surface (S) of the protruding portion 411. When the plastic shape setting film 301 is cooled it becomes rigid and the shape thereof is set and maintained. In this embodiment, the plastic shape setting film 301 is made of PET; however, in other embodiments, the plastic shape setting film 301 may be made of other thermal plastics. Furthermore, in this method, the optical film stack 302 has the back adhesive layer 33, the reflective layer 34, the optical layer 35, and the release layer 36. The back adhesive layer 33 of the optical film stack 302 is first adhered to the plastic shape setting film 301, then the plastic shape setting thin film 301 and the optical film stack 302 are heated and vacuum formed on the mold 4. In this embodiment, the optical film stack 302 is a multilayer high polymer film and has a plurality of optical elements 351 that are transparent beads. The optical elements 351 are formed by electrostatic spraying of molten glass through specialized nozzles to form droplets that solidify to form spherical glass beads due to surface tension.

Figure 9:
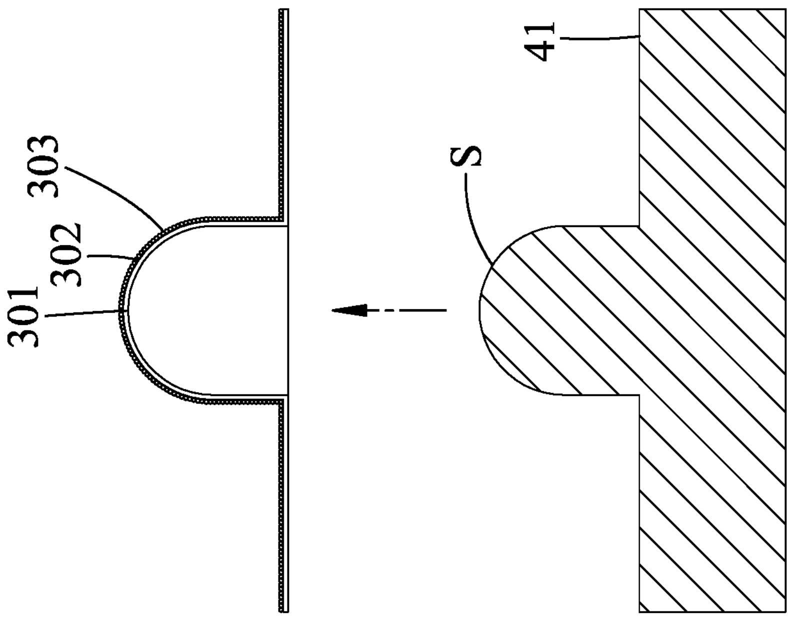

Referring to FIG. 9 in combination with FIGS. 7, 8, after cooling the laminate (M) of the plastic shape setting thin film 301 and the optical film stack 302, at least two semi-finished products 303 (only one is shown in FIG. 9) are formed. The vacuum formed laminate (M) is removed from the mold 41.

Figure 10:
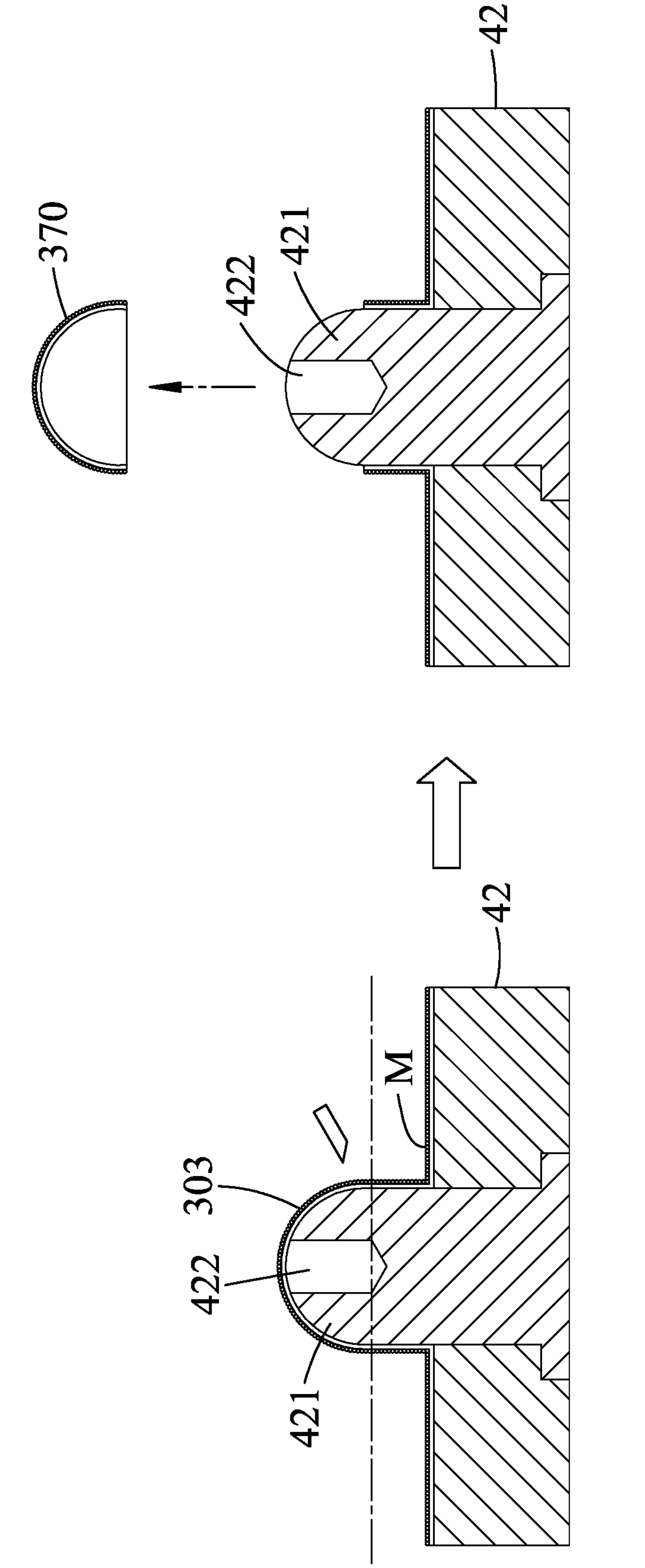
Figure 11:
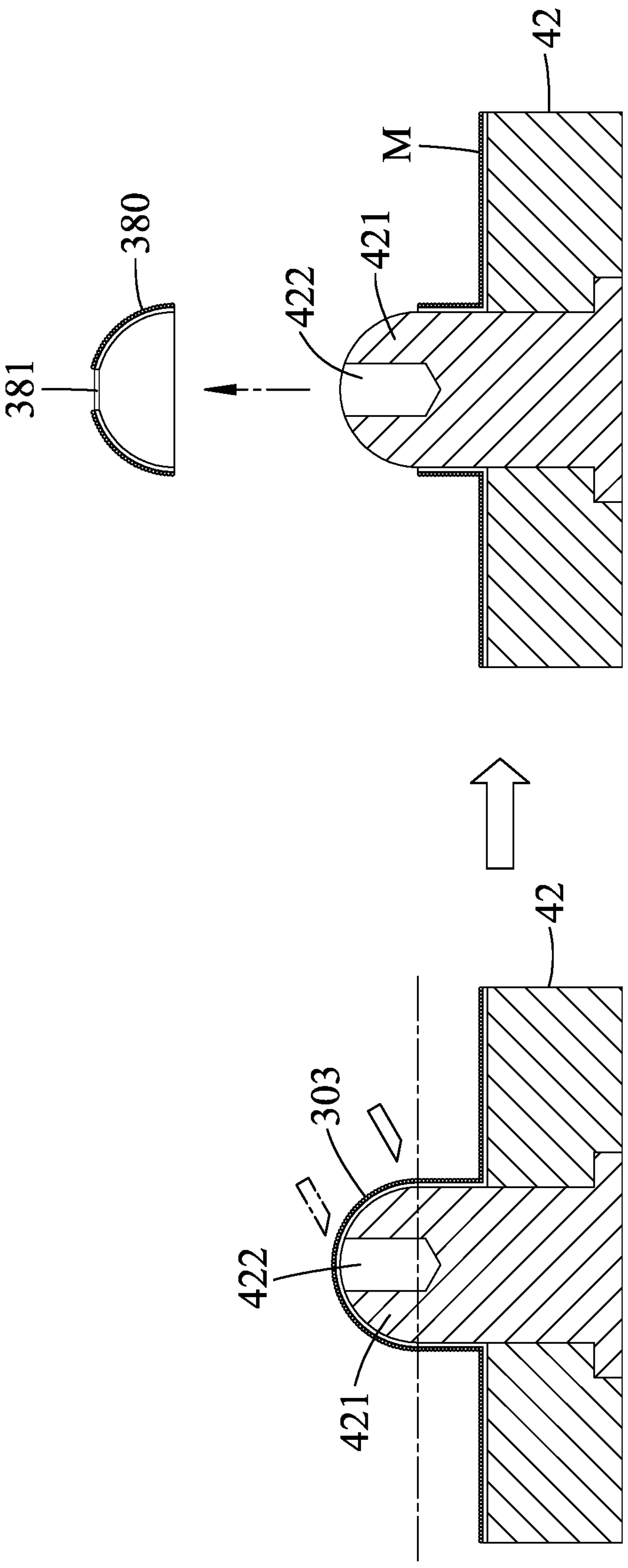

Referring to FIGS. 10 and 11 in combination with FIG. 7, in the step 92, the at least two semi-finished products 303 are cut off from the vacuum formed laminate (M) to respectively form first and second reflective shells 370, 380. To cut off the semi-finished products 303, first a cutting mold 42 is prepared. The cutting mold 42 has a protruding cutting portion 421 with a shape that matches the semi-finished product 303, and a machining hole 422 that is depressed from a top portion of the protruding cutting portion 421. As shown in FIG. 10, the vacuum formed laminate (M) is placed on the cutting mold 42 and the semi-finished product 303 is cut off from the vacuum formed laminate (M) with a machine cutter to form the first reflective shell 370. As shown in FIG. 11, this step is repeated for the other semi-finished product 303 to form the second reflective shell 380, and a through hole 381 is formed in the second reflective shell 380 directly above the machining hole 422 by using a cutting tool. Each of the first and second reflective shells 370, 380 has a designated shape, i.e., a dome-shape. In some embodiments, the through hole 381 is not formed with a machine cutter but is instead laser cut. It should be noted that the way in which the through hole 381 is formed is not a limitation of the disclosure. Because the shape setting film 301 have already been hardened and set, the optical film stack 302 is stably positioned and will not be torn or broken during machine cutting. This helps to preserve the physical integrity of the optical layer 35.

Figure 12:
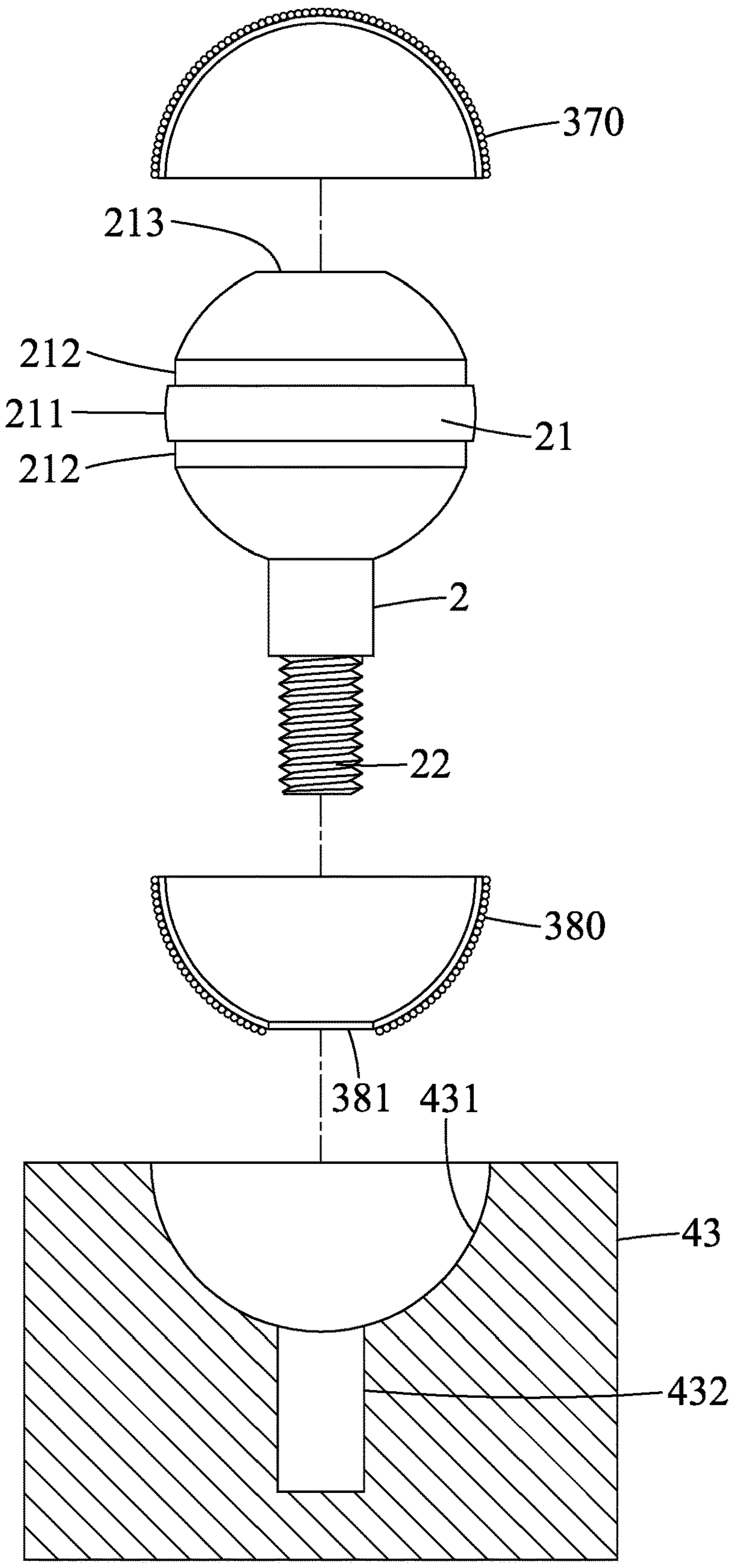

Referring to FIG. 7 in combination with FIG. 12, in the step 93, the main body unit 2 that has a ball body 21 and a rod portion 22 that extends outwardly from the ball body 21 is provided, and in the step 94, the ball body 21 is enwrapped with the first and second reflective shells 380. Each of the first reflective shell 370 and the second reflective shell 380 is adhered to an outer surface of the ball body 21 by adhesive bonding, while exposing the rod portion 22 of the main body unit 2. More specifically, a binding mold 43 that includes a cavity 431, and a slot 432 that extends from the cavity 431 is provided. The cavity 431 has a shape conforming to the exterior surface of the second reflective shell 380. The second reflective shell 380 is first placed in the cavity 431, and the through hole 381 of the second reflective shell 380 is aligned with the slot 432 of the binding mold 43. Next, a normal temperature adhesive (not shown) is applied to an inner surface of the second reflective shell 380. Subsequently, the main body unit 2 is lowered into the binding mold 43 with the rod portion 22 pointing downward. The rod portion 22 passes through the through hole 381 of the second reflective shell 380 and is inserted in the slot 432 of the binding mold 43. This allows the lower half of the ball body (21) to be adhered to the second reflective shell 380 in such a manner that the rod portion 22 of the main body unit 2 passes through the through hole 381 of the second reflective shell. In this step, because the rod portion 22 is aligned with the through hole 381 of the second reflective shell 380, the second reflective shell 380 will be correctly positioned on the lower half (P2) of the ball body 21, and allow the first reflective shell 370 to be accurately adhered later in the subsequent step of aligning peripheral rims of the first and second reflective shells 370, 380.

Next, the upper half (P1) of the ball body 21 is enwrapped with the first reflective shell 370 to form a positioning marker ball 100. A normal temperature adhesive (not shown) is applied to an inner surface of the first reflective shell 370, and the first reflective shell 370 is placed on the ball body 21 so that that the first reflective shell 370 is adhered to the upper half (P1) of the ball body 21. After performing this step a positioning marker ball 100 as shown in FIG. 4 is made. In the process of adhering the first and second reflective shells 370, 380 to the ball body 21, excess adhesive may fill into gaps formed between the ball body 21 and the inner surfaces of the first and second reflective shells 370, 380 at the depressions 212 and the top surface 213. This prevents excess adhesive material leaking out of the positioning marker ball 100. However, in other embodiments, the depressions 212 and the top surface 213 of the ball body 21 may be omitted, and the amount of adhesive use may be precisely controlled to prevent leakage. It is noted that, in this embodiment, the shape setting layer 32 is formed from the plastic shape setting film 301, and the optical layer 35 and the reflective layer 34 is formed from the optical film stack 302.

In some embodiments of the method for making the positioning marker ball 100, the normal temperature adhesive may be first applied to the outer surface of the ball body 21 and the first and second reflective shells 370, 380 are subsequently attached to form the positioning marker ball 100.

Figure 13:
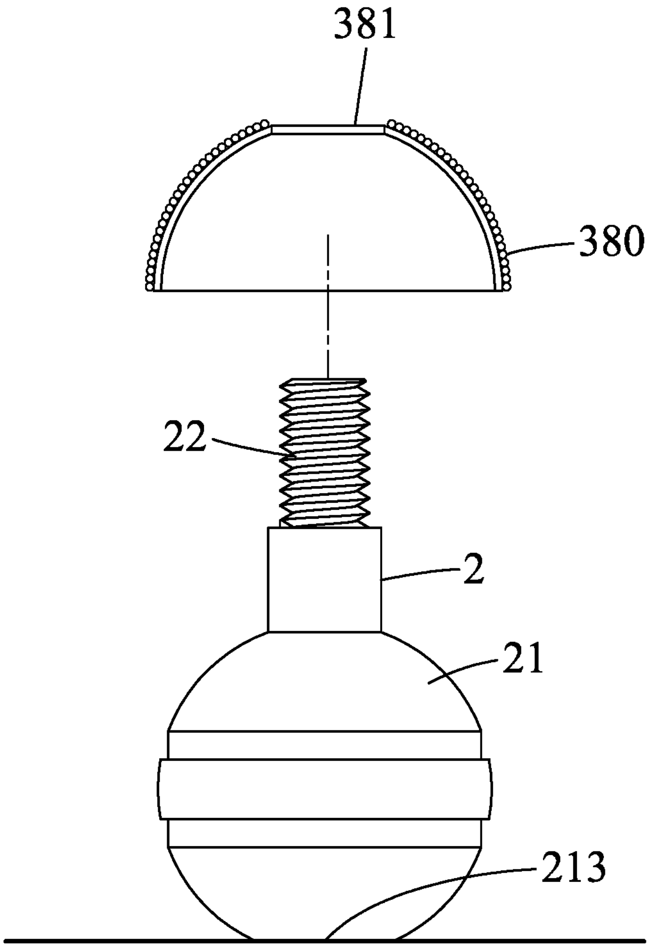
FIGS. 13 to 14 are schematic views illustrating a variation of the method for making the positioning marker ball of the first embodiment.
Figure 14:
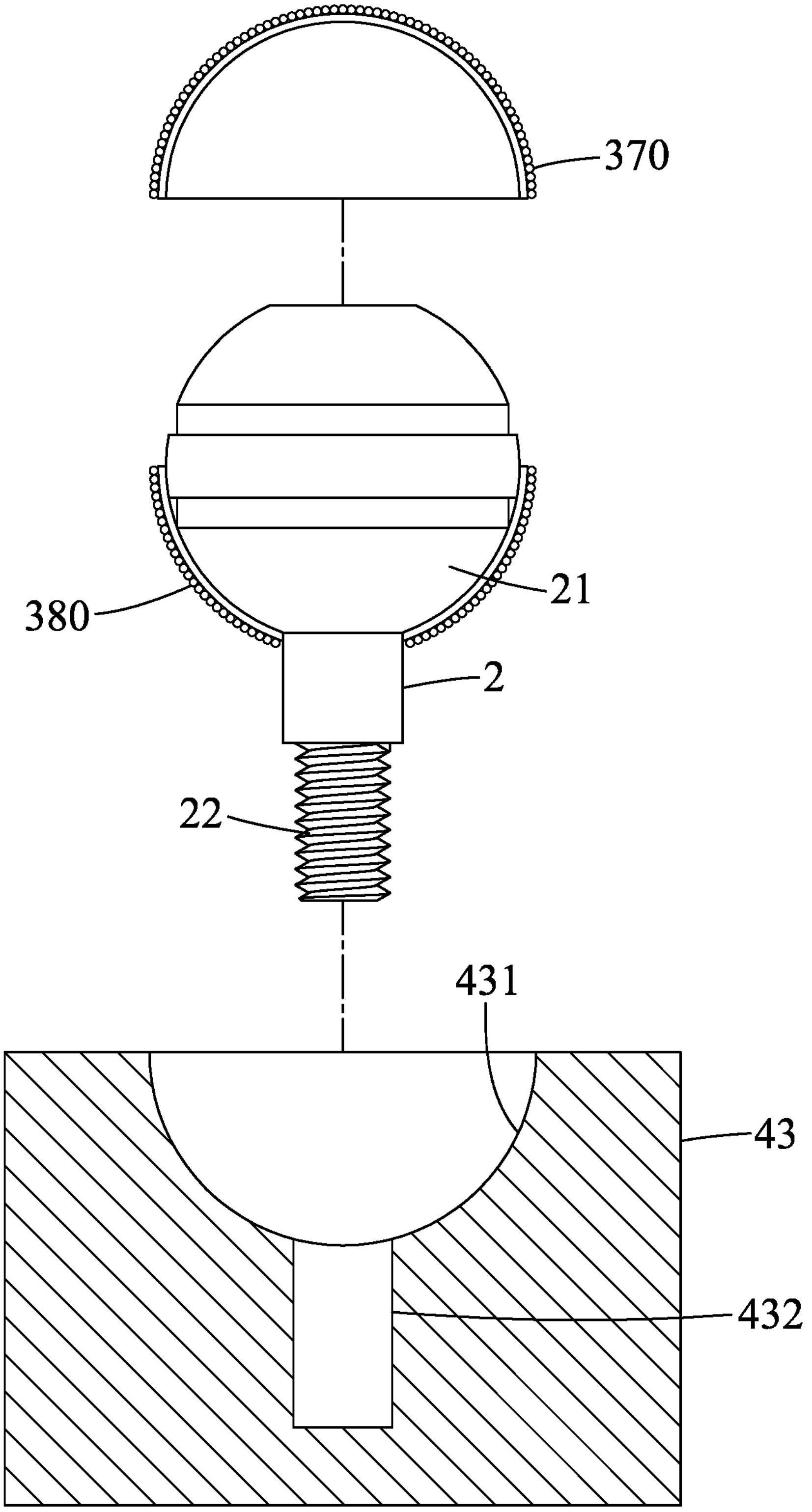

Referring to FIGS. 13 and 14, in a variation of the steps of enwrapping the ball body 21 of the main body unit 2 with the first and second reflective shells 370, 380, the main body unit 2 is placed on a table top with the top surface 213 of the ball body 21 in contact with the table top. This allows the main body unit 2 to be kept balancedly on the table top and prevent rolling of the main body unit 2. Next, the inner surface of the second reflective shell 380 is applied with an adhesive and the second reflective shell 380 is lowered onto the ball body 21 in such a manner that the rod portion 22 of the main body unit 2 passes through the through hole 381 of the second reflective shell 380, to adhere the second reflective shell 380 to the lower portion of the ball body 21. Referring to FIG. 14, the main body unit 2 is next lowered into the cavity 431 of binding mold 41 with the rod portion 22 of the main body unit 2 being inserted into the slot 432 of the binding mold 41. Then, the inner surface of the first reflective layer 370 is applied with an adhesive and lowered onto the upper portion of the ball body 21. It should be noted that in some embodiments, the binding mold 43 may be omitted as long as the first and second reflective shells 370, 380 are able to enwrap the ball body 21.

In the method of making the positioning marker ball 100, the plastic shape setting film 301 is a thermoplastic film that is pliable when heated, and can be laid on the protruding portion 411 of the mold 41 in conformity with the outer surface(S) of the protruding portion 411. The thermoplastic film is hardened when cooled and will allow the shape setting film 301 to set into the designated shape when cooled, and allow the first and second reflective shells 370, 380 to enwrap and conform to a contour of the ball body 21. The positioning marker ball 100 is therefore easy to manufacture.

It should be noted that the vacuum forming and heating, cutting, machining and adhesive bonding of the method described above may be subject to adjustments according to the practicalities of the situation and the current technical field, and should not be thus limited only to those described.

Additionally, in some embodiments of the positioning marker ball 100, the shape setting film 301 may be omitted, and the optical film stack 302 may be directly adhered to the ball body 21.

Figure 15:
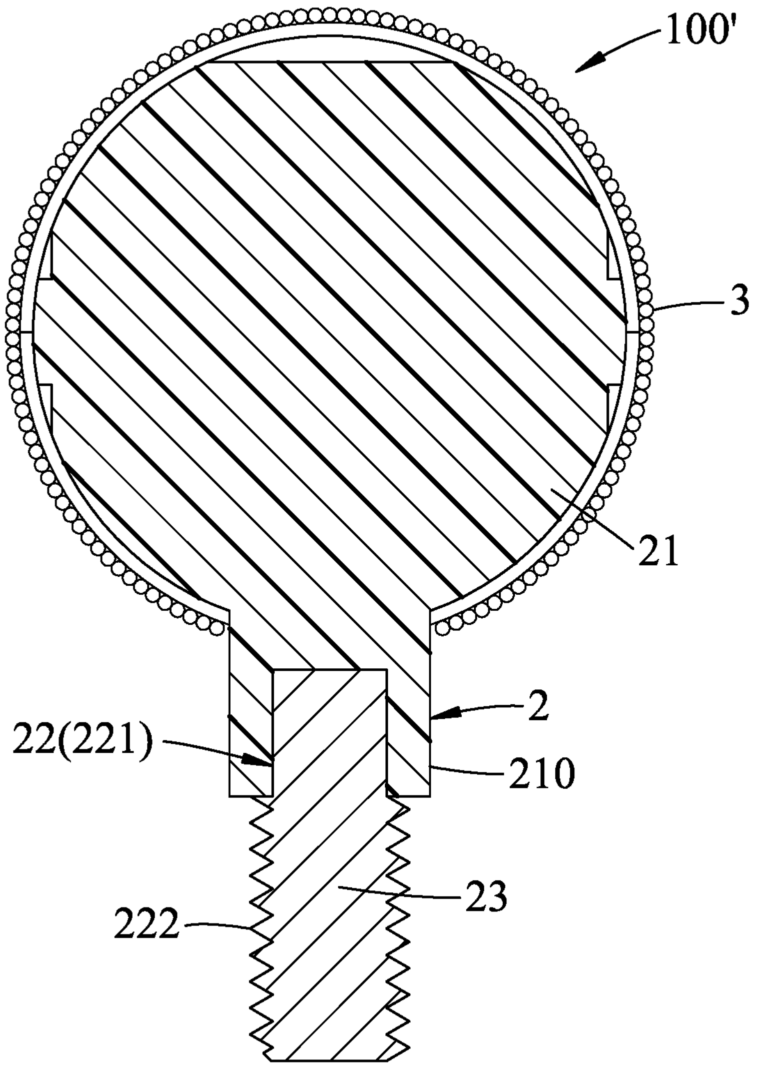
FIG. 15 is a cross sectional view illustrating a second embodiment of a positioning marker ball according to the present disclosure.

Referring to FIG. 15, a second embodiment of the positioning marker ball 100' according to the present disclosure is similar to the first embodiment. However, the second embodiment is different in that the ball body 21 is made of a polycarbonate (PC) plastic, the rod portion 22 is made of metal, and the ball body 21 and the rod portion 22 are integrally formed via insert molding. Specifically, the rod portion 22 that has the interconnection section 221 and the connecting end section 222 is a stainless steel rod, more specifically, a stainless steel screw rod 23, and the PC plastic ball body 21 is insert molded with the stainless steel screw rod 23. After insert molding, the ball body 21 has a tubular sleeve portion 210 projecting outwardly from the outer surface of the ball body 21 in line with an axial line of the ball body 21. The interconnecting section 221 of the rod portion 22 is embedded in the tubular sleeve portion 210.

Another embodiment of the method for making the positioning marker ball 100 includes forming the optical unit 3 on the ball body 21 of the main body unit 2. More specifically, the ball body 21 of the main body unit 2 is spray painted with a coarse grained material to roughen the surface of the ball body 21. Next, a reflective layer 34 of the optical unit 3 is formed by spraying the roughened surface of the ball body 21 with a reflective material. A positioning marker ball 100 made with this method may reflect light and have increased visibility.

Figure 16:
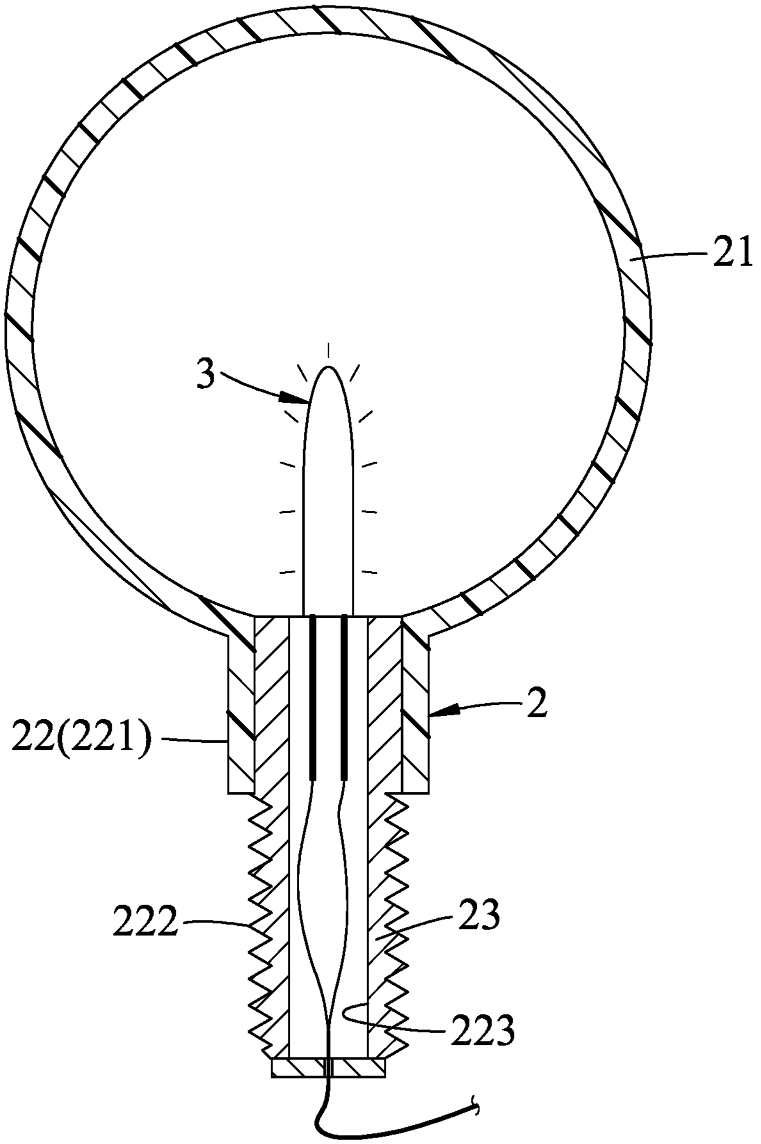
FIG. 16 is a schematic cross sectional view illustrating a third embodiment of a positioning marker ball according to the present disclosure.

Referring to FIG. 16, a third embodiment of the positioning marker ball 100" includes a main body unit 2, and an optical unit 3. The main body unit 2 includes a ball body 21 that is transparent and hollow, and a rod portion 22 that extends outwardly form the ball body 21, and that has a connecting end portion 221 disposed opposite the ball body 21 and adapted to connect a mount. The ball body 21 is molded integrally with the rod portion 22. The rod portion 22 is hollow and has a passage hole 223 spatially communicating an interior of the ball body 21. The optical unit 3 has a light source (30) mounted inside the ball body 21 of the main body unit 2 and is adapted to connect a power source through the passage hole 223. In this embodiment the light source 30 may be a light-emitting diode (LED) that emits light when connected to a power source.

In summary of the above, in the positioning marker ball 100, 100', 100" according to the present disclosure, the ball body 21 is molded integrally with the rod portion 22. Therefore, the ball body 21 will not loosen, rattle, or fall apart from the rod portion. Additionally, this design increases the structural strength of the positioning marker ball 100, and increases the safety of the positioning device 101. In some embodiments, the plastic shape setting film 301 is a thermoplastic film that is pliable when heated and that can be hardened when cooled for setting into a designated shape. Because of this, the first and second reflective shells 370, 380 may be maintained in their shapes to closely conform to the outer surface of the ball body 21. This has the advantage of increasing the ease of manufacture.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A positioning marker ball adapted for an optical positioning system comprising:
- a main body unit including
  - a ball body, and
  - a rod portion that extends outwardly from said ball body, and that has a connecting end section disposed opposite said ball body and adapted to connect a mount, said ball body being molded integrally with said rod portion, and an optical unit disposed on said ball body, and including
  - a reflective layer that is disposed on the ball body, and that reflects light;
- wherein said optical unit further includes an optical layer that is disposed on an outer surface of said ball body, and that has a plurality of optical elements that allow passage of light therethrough; and
- wherein said optical unit further includes a shape setting layer that is made of thermoplastic, and that is formed between said optical layer and said ball body.

2. The positioning marker ball as claimed in claim 1, wherein said main body unit is entirely made of aluminum or an aluminum alloy.

3. The positioning marker ball as claimed in claim 1, wherein:
- said rod portion further has an interconnecting section that is opposite to said connecting end section and that interconnects with said ball body; and
- said ball body is made of plastic, said rod portion being made of metal, and said ball body being integrally molded with said rod portion via insert molding.

4. The positioning marker ball as claimed in claim 3, wherein said ball body has a tubular sleeve portion projecting outwardly from said outer surface of said ball body and being in line with an axial line of said ball body, said interconnecting section of said rod portion being embedded in said tubular sleeve portion.

5. The positioning marker ball as claimed in claim 1, wherein said reflective layer is formed between said optical layer and said shape setting layer.

6. The positioning marker ball as claimed in claim 1, wherein said optical elements are transparent beads.

7. The positioning marker ball as claimed in claim 1, wherein said optical unit further includes a first reflective shell covering and adhesively bonded to a first portion of said outer surface of said ball body, and a second reflective shell covering and adhesively bonded to a remaining second portion of said outer surface of said ball body, said first and second reflective shells being convex and complementarily forming a ball-shaped shell, each of said first and second reflective shells having said reflective layer that is disposed on said ball body.

8. The positioning marker ball as claimed in claim 7, wherein said ball body has an equatorial line dividing said outer surface of said ball body into said first portion and said remaining second portion, and two depressions which sink inwardly from said outer surface of said ball body and are respectively formed in said first portion and said remaining second portion.

9. The positioning marker ball as claimed in claim 7, wherein each of said first and second reflective shells further has said optical layer that is laminated with said reflective layer said reflective layer being disposed between said optical layer and said ball body.

10. The positioning marker ball as claimed in claim 9, wherein each of said first and second reflective shells further has said shape setting layer that is disposed between said reflective layer and said ball body.

11. A positioning device adapted for an optical positioning and tracking system comprising:
- a mount including a plurality of threaded holes; and
- a plurality of positioning marker balls each of which is said positioning marker ball as claimed in claim 1;
- wherein said connecting end section of each of said positioning marker balls is coupled with one of said threaded holes of said mount.

* * * * *